United States Patent
Korrapati et al.

(10) Patent No.: US 8,106,216 B2
(45) Date of Patent: Jan. 31, 2012

(54) PROCESS FOR THE PREPARATION OF IRBESARTAN

(75) Inventors: Venkata vara prasada rao Korrapati, Hyderabad (IN); Venkata subramanyeswara rao Inti, Hyderabad (IN); Rani Ananta, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 61 days.

(21) Appl. No.: 11/795,896

(22) PCT Filed: Apr. 23, 2007

(86) PCT No.: PCT/IB2007/001092
§ 371 (c)(1),
(2), (4) Date: Nov. 9, 2009

(87) PCT Pub. No.: WO2007/122508
PCT Pub. Date: Nov. 1, 2007

(65) Prior Publication Data
US 2010/0056797 A1    Mar. 4, 2010

(30) Foreign Application Priority Data

Apr. 24, 2006 (IN) .............................. 745/CHE/2006
Aug. 28, 2006 (IN) ........................... 1540/CHE/2006
Apr. 16, 2007 (IN) .............................. 800/CHE/2007

(51) Int. Cl.
*C07D 235/02* (2006.01)
*C07D 257/02* (2006.01)
(52) U.S. Cl. .................... 548/253; 548/300.7
(58) Field of Classification Search ................. 548/253, 548/300.7
See application file for complete search history.

(56) References Cited

U.S. PATENT DOCUMENTS

| 5,270,317 | A | 12/1993 | Bernhart et al. |
| 5,559,233 | A | 9/1996 | Bernhart et al. |
| 7,038,060 | B2 | 5/2006 | Dolitzky et al. |
| 2009/0286990 | A1 | 11/2009 | Reddy et al. |

FOREIGN PATENT DOCUMENTS

| WO | WO 2005/051943 A1 | 6/2005 |
| WO | WO 2005/113518 | * 12/2005 |

OTHER PUBLICATIONS

Claude A et al., "Highly Specific and Potent Nonpeptide AT1 Angiotensin II Receptor Antagonists" Journal of Medicinal Chemistry (1993), 36(22), 3371-80.

* cited by examiner

*Primary Examiner* — Susannah Chung
(74) *Attorney, Agent, or Firm* — Jay R Akhave

(57) ABSTRACT

The present invention relates to an improved process for the preparation of 2-n-butyl-3-[[2'-(1H-tetrazol-5-yl)[1,1'-biphenyl]-4-yl]-1,3-diazaspiro[4.4]non-1-en-4-one (Irbesartan).

12 Claims, No Drawings

PROCESS FOR THE PREPARATION OF IRBESARTAN

This application claims the priority from Indian Application Nos. 745/CHE/2006, 1540/CHE/2006 and 800/CHE/2007 filed on Apr. 24, 2006, Aug. 28, 2006 and Apr. 16, 2007 respectively and entitled "AN IMPROVED PROCESS FOR THE PREPARATION OF IRBESARTAN", which is incorporated by reference herein in its entirety.

FIELD OF THE INVENTION

The present invention relates to an improved process for the preparation of 2-butyl-3-[p-(o-1H-tetrazol-5-ylphenyl)benzyl]-1,3-diazaspiro[4.4]non-1-en-4-one of Formula I Formula I

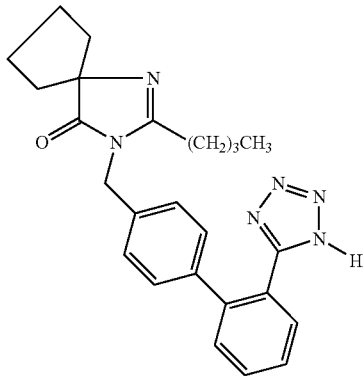

BACKGROUND OF THE INVENTION

2-Butyl-3-[p-(o-1H-tetrazol-5-ylphenyl)benzyl]-1,3-diazaspiro[4.4]non-1-en-4-one, is generically known as Irbesartan. Irbesartan is a non-peptide angiotensin II antagonist, which antagonizes the physiologic effects of angiotensin II by inhibiting the action of angiotensin II on its receptors, the compounds particularly prevent increase in blood pressure produced by the receptor interaction. Irbesartan is approved for the treatment of hypertension and is marketed in the US with the Brand Name, Avapro.

Elf Sanofi, first time disclosed Irbesartan and its pharmaceutically acceptable salts in U.S. Pat. No. 5,270,317.

U.S. Pat. No. 5,399,578 describes two different processes for the preparation of Irbesartan which are subsequently claimed in U.S. Pat. No. 5,559,233. One of the processes involves the reaction of 2-n-butyl-4-spirocyclopentane-2-imidazolin-5-one (II) with 4-bromomethyl-2-cyanobiphenyl (III) in the presence of NaH, followed by a column chromatography separation to yield 1-[(2'-cyanobiphenyl-4-yl)methyl]-2-n-butyl-4-spirocyclopentane-2-imidazolin-5-one (IV). This compound (IV) is further reacted with tributyltin azide and the product treated with trityl chloride and separated by column chromatography. Finally, trityl protected irbesartan (V) is de-protected with hydrochloric acid and the final Irbesartan product is isolated.

The process is as shown in Scheme-I:

Scheme I:

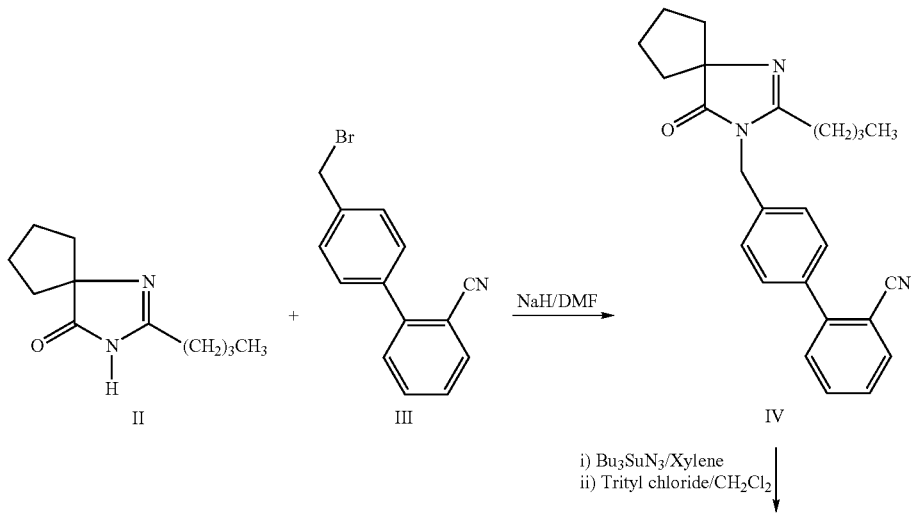

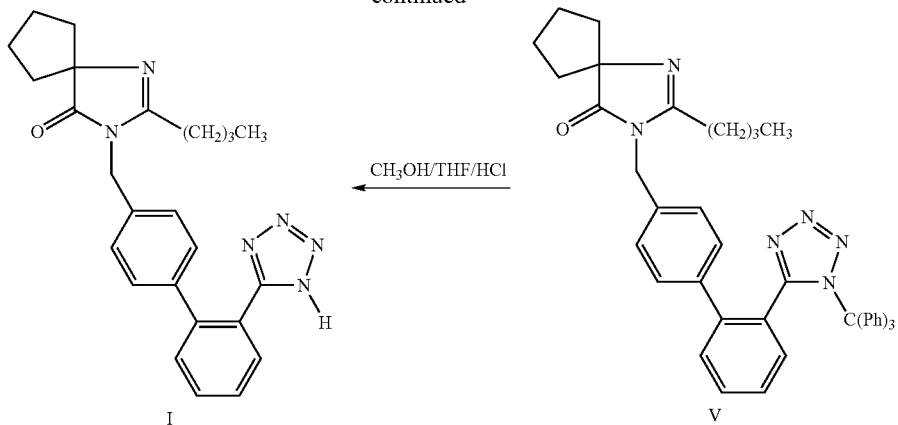
The second process described in this patent for the preparation of Irbesartan, is as shown in Scheme-II:
Scheme II:
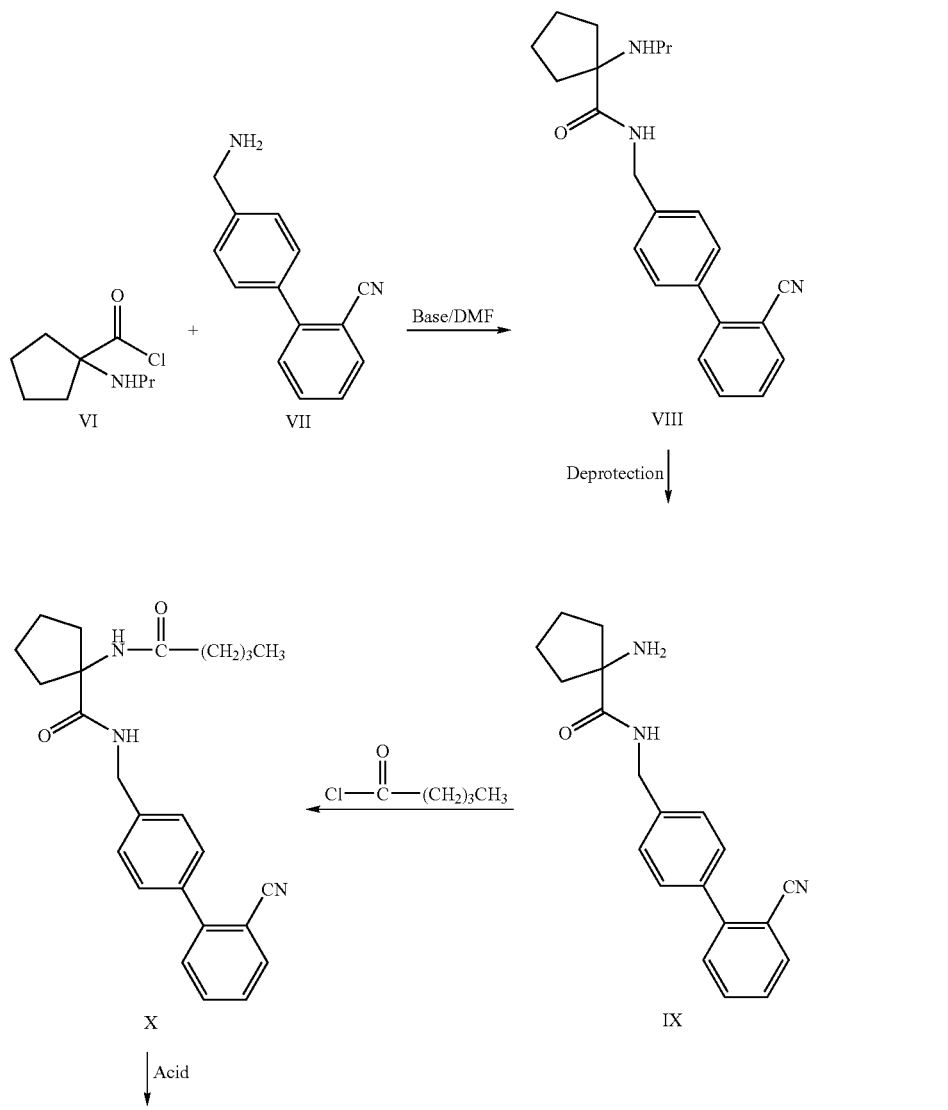

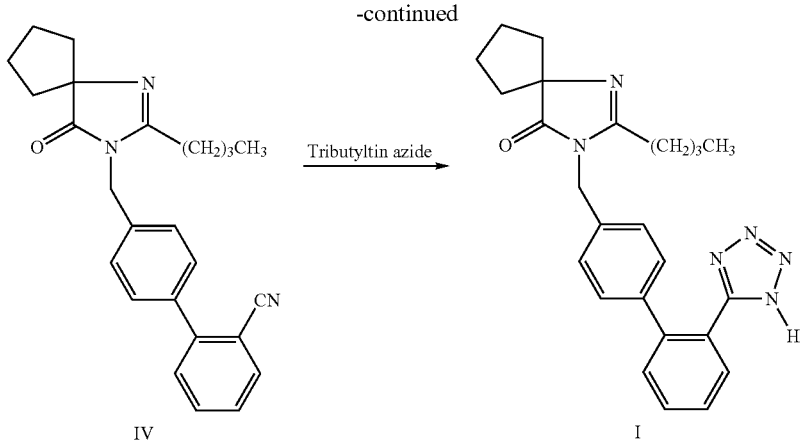

The major disadvantages with the above processes for the preparation of Irbesartan, involve a large number of steps such as protection and deprotection and tedious work-up procedures to isolate the required product. This results in more production time, which in turn renders the process more costly and less eco friendly. Further the above processes are low yielding and yield product of less purity.

WO 2005/113518 A1 describes an alternative process for the preparation of Irbesartan which involves reacting N-pentanoylaminocyclopentanecarboxylic acid (XI) with 2-(4-aminomethylphenyl)benzonitrile (VII) using dicyclohexylcarbodiimide and 1-hydroxybenzotriazole as a catalyst to produce the 4-[(α-N-pentanoylamino)cyclopentamidomethyl]-2-cyanobiphenyl (XII), and then cyclizing using trifluoroacetic acid to result 1-[(2'-cyanobiphenyl-4-yl)methyl]-2-n-butyl-4-spirocyclopentane-2-imidazolin-5-one (IV), which is finally converted to Irbesartan (I) by reaction with tributyl tin chloride and sodium azide.

The process is as shown in Scheme-III below:

Scheme III:

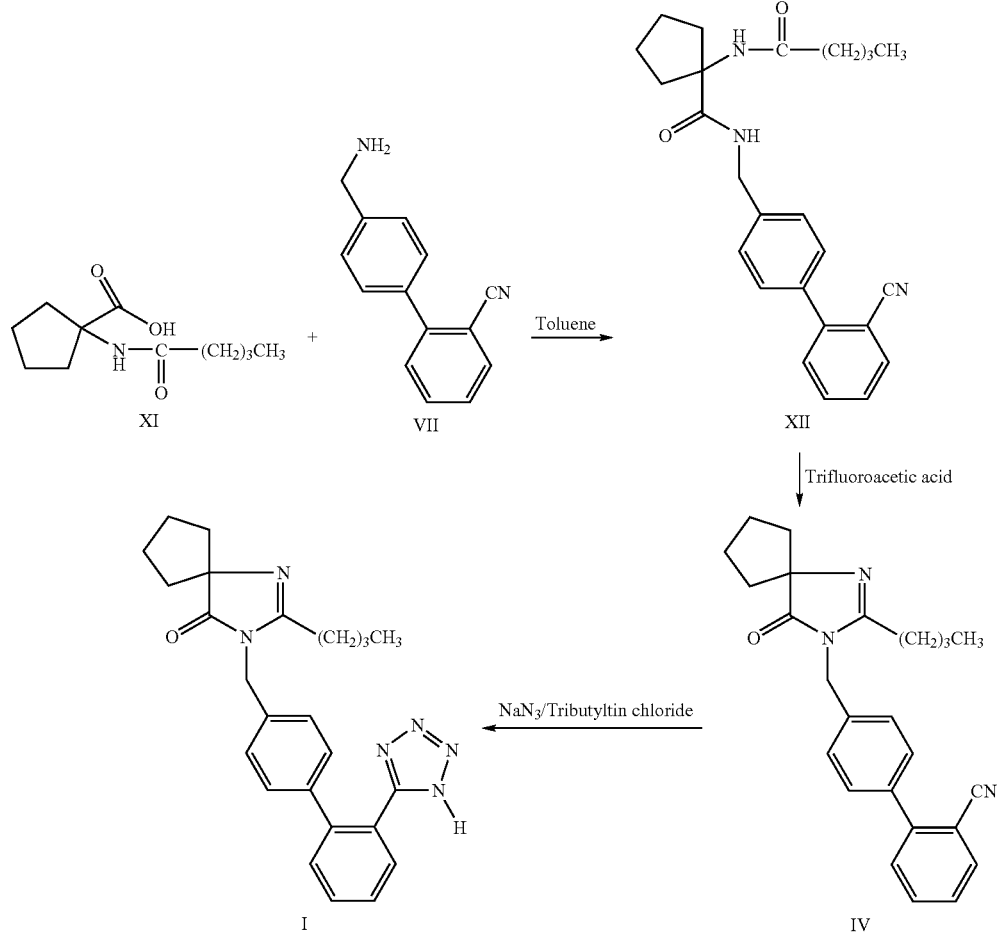

We have now developed another process to prepare Irbesartan, which is novel and commercially viable process.

OBJECTIVE OF INVENTION

The main objective of the present invention is to provide a simple, effective and industrially feasible process for the preparation of Irbesartan with high purity and good yields on a commercial scale.

SUMMARY OF THE INVENTION

Accordingly, the present invention relates to an improved process for the preparation of 2-butyl-3-[p-(o-1H-tetrazol-5-ylphenyl)benzyl]-1,3-diazaspiro[4.4]non-1-en-4-one (Irbesartan) of Formula (I), Formula I

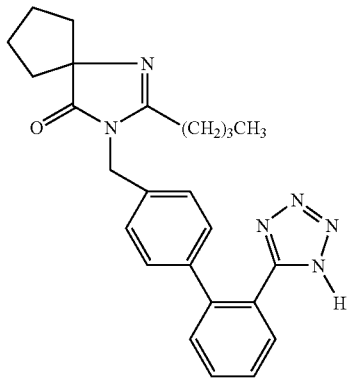

which comprises:
i) reacting the compound of Formula (XVI)

Formula XVI

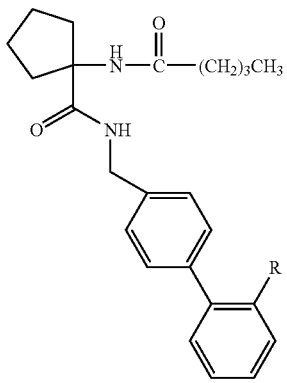

wherein R represents —CN and —CONH$_2$ groups
with trialkyltin chloride and alkaline azide in an organic solvent to produce compound of Formula I.

In another embodiment, the present invention also relates to a process for the preparation of a compound of Formula (XVI)

Formula XVI

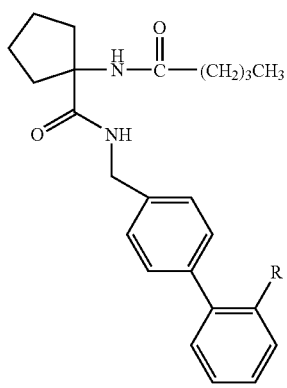

where R represents —CN and —CONH$_2$
which comprises:
i) condensing the compound of Formula (XVII) or (XIIIa) with N-pentanoylaminocyclopentanecarboxylic acid of Formula (XI)

Formula XI

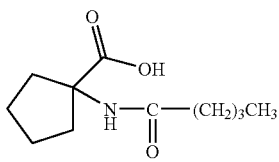

in presence of a condensing agent and optionally using a base in a solvent to produce compound of Formula (XVI)

In another embodiment, the present invention also relates to a process for the preparation of 4-aminomethyl-1,1-biphenyl-2'-carboxamide of Formula (XIIIa)

Formula XIIIa

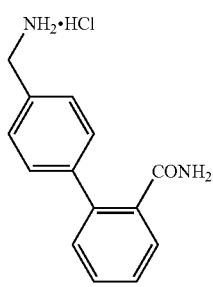

which comprises:
i) converting 4-aminomethyl-2-cyanobiphenyl hydrochloride of Formula XVII

XVII

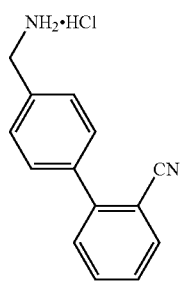

to 4-aminomethyl-1,1'-biphenyl-2'-carboxamide hydrochloride of Formula XIIIa in presence of a base in tert. butanol and ii) isolating the compound of Formula (XIIIa) as a hydrochloride salt.

In another embodiment, the present invention relates to an improved process for the preparation of 2-n-butyl-3-[[2'-(1H-tetrazol-5-yl)[1,1'-biphenyl]-4-yl]-1,3-diazaspiro[4.4]non-1-en-4-one (Irbesartan) of Formula (I), Formula I

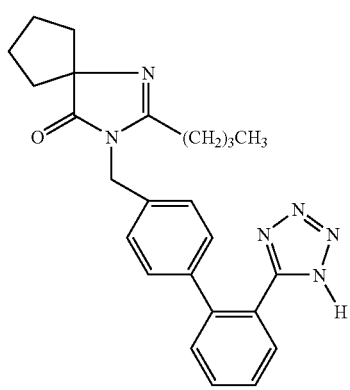

which comprises, i) condensing the compound (XI)

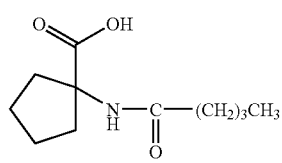

Formula XI with 4-aminomethyl-1,1'-biphenyl-2'-carboxamide (XIII);

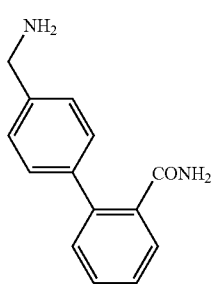

Formula XIII in presence of condensing agent and optionally using a base in a solvent to produce 4-[(α-N-pentanoylamino)cyclopentamidomethyl]-2'-carboxamidobiphenyl (XIV), Formula XIV

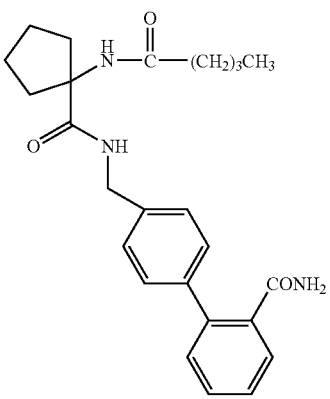

ii) cycling a compound (XIV) in presence of acid in a solvent to produce 1-[(2'-carboxamidobiphenyl-4-yl)methyl]-2-n-butyl-4-spirocyclopentane-2-imidazolin-5-one (XV), Formula XV

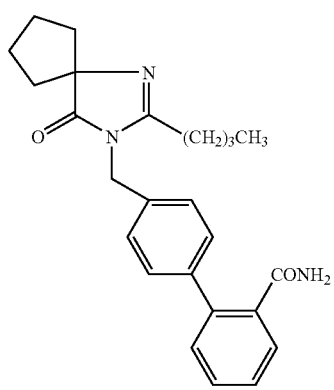

iii) converting the compound (XV) to Irbesartan (I).

DETAILED DESCRIPTION OF THE INVENTION

The present invention relates to an improved process for the preparation of 2-butyl-3-[p-(o-1H-tetrazol-5-ylphenyl)benzyl]-1,3-diazaspiro[4.4]non-1-en-4-one (Irbesartan) of Formula (I).

The compound of Formula (XVI) wherein R represents —CN and —CN and —CONH$_2$ groups can be cyclized to form Irbesartan. The compound of Formula (XVI) is treated with trialkyltin chloride such as tributyltin chloride and alkaline azide selected from sodium azide, potassium azide in a solvent selected from aromatic hydrocarbons such as benzene, toluene, xylene, polar aprotic solvent such as dimethylformamide, N-methylpyrrolidinone and mixtures there of, more preferably mixture of dimethylformamide and o-xylene. The reaction mixture is heated to 150-155° C. and after completion of reaction, the reaction mass is cooled to about 20° C. o-Xylene and methylene chloride are added to the reaction mass followed by water. Subsequently hydrochloric acid is added at 20-25° C. slowly over a period of 30 min and the slurry obtained was stirred for 60 min. The precipitated solid was filtered and washed with a mixture of o-xylene and methylene chloride and dried to give compound of Formula I.

The compound of Formula (XVII) i.e. 4-aminomethyl-2'-cyanobiphenyl hydrochloride (XVII) is converted to compound of Formula (XIIIa) using a base selected from sodium hydroxide or potassium hydroxide in t-butanol as a solvent. In a preferred procedure, the compound of Formula (XVII) is suspended in a mixture of water and methylene chloride, and the pH of the suspension is adjusted to 9.0-9.5 with ammonium hydroxide to get a clear solution. The organic layer is separated, concentrated and to the resulting mass tert. butanol is added, followed by addition of powdered potassium hydroxide at 70-75° C., the reaction mixture is heated to reflux for completion. After completion of the reaction, water is added and the product extracted with methylene chloride and thereafter the pH of the methylene chloride layer is adjusted to 1.2-1.4 with hydrochloric acid wherein the compound of Formula (XIIIa) precipitates out as a hydrochloride salt.

The compound of formula (XVI) wherein R represents —CN and —CONH$_2$ groups can be prepared by condensing N-Pentanoylaminocyclopentanecarboxylic acid (XI) with 4-aminomethyl-1,1'-biphenyl-2'-carboxamide hydrochloride (XIIIa) in presence of base selected from, triethylamine, diethylamine, N,N-diisopropylethylamine, preferably diisopropylethylamine in a solvent selected from dimethylformamide, dimethylacetamide, dimethylsulfoxide, acetone and chlorinated hydrocarbon such as methylene chloride, chloroform, 1,2-dichloroethane, preferably methylene chloride. Condensation is carried out in presence of condensing agent such as N,N'-dicyclohexylcarbodiimide, N-hydroxysuccinimide and a catalyst selected from 1-hydroxybenzotriazole at a temperature of about 20° C. to about 40° C. Condensation can also be carried out without using base. After completion of reaction, as ascertained by the known detection methods such as HPLC/TLC, the reaction mass is cooled to room temperature and filtered. The filtrate is washed with saturated sodium bicarbonate solution and the solvent evaporated to ¼$^{th}$ volume. The obtained solid is cooled to 0-5° C. and filtered to give compound of Formula (XVI).

Similarly, the compound of Formula (XVII) is condensed with N-pentanoylaminocyclopentanecarboxylic acid (XI) employing the same reaction conditions described as above to result in compound of Formula (XVI). This condensation of compound of Formula (XVII) with compound of Formula (XI) to give compound of Formula (XVI). This condensation of compound of Formula (XVII) with compound of Formula (XI) to give compound of Formula (XVI) is a significant improvement over the prior-art methods, which has hitherto not been reported. By using compound of Formula (XVII), Irbesartan can thus be produced in two steps only which consist of condensing with compound of Formula (XI) and subsequent cyclization of the resulting compound of Formula (XVI) to yield compound of Formula I.

The compound of Formula (XVII) is prepared by known methods in literature.

In another embodiment, N-pentanoylaminocyclopentanecarboxylic acid (XI) is condensed with 4-aminomethyl-1,1'-biphenyl-2'-carboxamide (XIII) in presence of base selected from triethylamine, diethylamine, diisopropylethylamine, preferably diisopropylethylamine in a solvent selected from chlorinated hydrocarbon such as methylene chloride, chloroform, 1,2-dichloroethane, preferably methylene chloride. Condensation is carried out in presence of condensing agent such as N,N'-dicyclohexylcarbodiimide, N-hydroxysuccinamide and a catalyst selected from 1-hydroxybenzotriazole at a temperature of about 20° C. to about 40° C. Condensation can also be carried out without using base. After completion of reaction as ascertained by the known detection methods reported in the art, such as HPLC/TLC, cool the reaction mass to 0-5° C. and filter the unwanted salts. The filtrate is washed with saturated sodium bicarbonate solution and evaporates the solvent to ¼$^{th}$ volume and filter the obtained solid 4-[(α-N-pentanoylamino)cyclopentamidomethyl]-2'-carboxamidobiphenyl (XIV).

4-[(α-N-pentanoylamino)cyclopentamidomethyl]-2'-carboxamidobiphenyl (XIV) is cyclised in presence of acid selected from trifluoroacetic acid, trifluoromethanesulfonic acid, p-toluenesulfonic acid, trifluoromethanesulfonic anhydride in a solvent selected from aromatic hydrocarbons such as benzene, toluene, xylene. The cyclisation reaction is carried out at a temperature of about 120° C. to about 150° C., preferably at about 135° C. to about 140° C. After completion of reaction as ascertained by the known detection methods reported in the art, solvent is removed under reduced pressure and added a solvent selected from ethylacetate, methylene chloride. pH of the reaction mass is adjusted to about 9.0 using a base selected from sodium hydroxide, potassium hydroxide or ammonium hydroxide. Separate the organic layer and distill out the solvent and added second solvent selected from toluene and cool the slurry. Filter the solid to obtain 1-[(2'-carboxamidobiphenyl-4-yl)methyl]-2-n-butyl-4-spirocyclopentane-2-imidazolin-5-one (XV).

Treating 1-[(2'-carboxamidobiphenyl-4-yl)methyl]-2-n-butyl-4-spirocyclopentane-2-imidazolin-5-one (XV) with acid chloride selected from p-toluenesulfonylchloride, benzenesulfonyl chloride, thionyl chloride in presence of organic base selected from pyridine. When the reaction is carried out in presence of a base, the reaction proceeds through a cyano intermediate, which may or may not be isolated. The reaction is carried out at a temperature of about 50° C. to about 80° C. for 1 hr to about 3 hrs, most preferably 1 hr. After completion of reaction, the reaction mass is diluted with ethylacetate and water and stir for 15 minutes. Separate the organic layer and distill out the ethyl acetate completely and add fresh ethyl acetate and keep it for overnight to produce a crystalline 1-[(2'-Cyanobiphenyl-4-yl)methyl]-2-n-butyl-4-spirocyclopentane-2-imidazolin-5-one (IV).

1-[(2'-Cyanobiphenyl-4-yl)methyl]-2-n-butyl-4-spirocyclopentane-2-imidazolin-5-one (IV) is treated with trialkyl tin chloride selected from tributyl tin chloride and alkyl azide selected from sodium azide, potassium azide in a solvent selected from aromatic hydrocarbons selected from benzene, toluene, xylenes, most preferably o-xylene. The reaction is carried out at reflux temperature for about 20 to 24 hrs. After completion of reaction as ascertained by the known detection methods reported in the art, cool the reaction mass to about 15° C. to 30° C., preferably 15° C. to 20° C. and Water, followed by hydrochloric acid is added and stir the reaction mass for 10 to about 30 minutes. Filter the solid and suspended in water, adjust the pH to 12.0 using inorganic base selected from sodium hydroxide, potassium hydroxide or ammonium hydroxide. Wash the resulting solution with solvent selected from ethyl acetate, methylene acetate, butylacetate, and adjust the pH of the aqueous layer to 4.6 to 4.8 using hydrochloric acid. The solid obtained is filtered to produce crude Irbesartan of Formula I.

In another embodiment, Irbesartan can be prepared without isolating intermediate 1-[(2'-Cyanobiphenyl-4-yl)methyl]-2-n-butyl-4-spirocyclopentane-2-imidazolin-5-one (IV). After completion of reaction of compound XV with acid chloride, the reaction mass is diluted with solvent selected from aromatic hydrocarbons such as toluene, benzene, xylenes and water and separate the organic layer. Treating organic layer containing 1-[(2'-Cyanobiphenyl-4-yl)methyl]-2-n-butyl-4-spirocyclopentane-2-imidazolin-5-one (IV), with trialkyl tin chloride selected from tributyl tin chloride and alkyl azide selected from sodium azide, potassium azide in a solvent selected from aromatic hydrocarbons selected from benzene, toluene, xylenes, most preferably o-xylene. The reaction is carried out at reflux temperature for about 20 to 24 hrs. After completion of reaction as ascertained by the known detection methods reported in the art, cool the reaction mass to about 15° C. to 30° C., preferably 15° C. to 20° C. and Water, followed by hydrochloric acid and stirring the reaction mass for 10 to about 30 minutes. Filter the solid and suspended in water, adjust the pH to 12.0 using inorganic base selected from sodium hydroxide, potassium hydroxide, and ammonium hydroxide. The resulting solution is washed with the solvent selected from ethyl acetate, methyl acetate, butyl acetate and adjusts the pH of the aqueous layer to 4.6 to 4.8 using hydrochloric acid. The solid obtained is filtered to produce crude Irbesartan of Formula I.

In an another embodiment, alternatively one can also proceed directly for preparation of Irbesartan by reacting 1-[(2'-carboxamidobiphenyl-4-yl)methyl]-2-n-butyl-4-spirocyclopentane-2-imidazolin-5-one (XV) with trialkyl tin chloride selected from tributyl tin chloride and alkyl azide selected from sodium azide, potassium azide in a solvent selected from aromatic hydrocarbons selected from benzene, toluene, xylenes, most preferably o-xylene. The reaction is carried out at reflux temperature for about 20 to 24 hrs. After completion of reaction, as ascertained by the known detection methods reported in the art, the reaction mass is cooled to about 15° C. to 30° C., preferably 15° C. to 20° C. and methylene chloride o-xylene and water were added followed by hydrochloric acid and stir the reaction mass for about 60 minutes. The solid precipitated is filtered and suspended in water, the pH is adjusted to 12.0 using inorganic base selected from sodium hydroxide, potassium hydroxide or ammonium hydroxide. The resulting solution is washed with solvent selected from ethyl acetate, methyl acetate, butylacetate, and the pH of the aqueous layer is adjusted to 4.6 to 4.8 using hydrochloric acid. The solid obtained is filtered to produce crude Irbesartan of Formula I.

Crude Irbesartan I, is purified by suspending in a solvent selected from alcohols such as methanol, ethanol, isopropanol, butanol at reflux temperature to get a solution and is treated with carbon. The filtrate is cooled to 10° C.-15° C., filtering the solid obtained, followed by drying to produce pure Irbesartan The following examples to prepare Irbesartan illustrate the nature of the invention and are provided for illustrative purpose only and should not be construed to limit the scope of the invention.

Example I

Stage I: Preparation of 4-Aminomethyl-1,1'-biphenyl-2'-carboxamide hydrochloride (XIIIa)

4-Aminomethyl-2'-cyanobiphenyl hydrochloride (XVII) (100 g, 0.408 mole) was suspended in a mixture of water (500 ml) and methylene chloride (200 ml) at 25-30° C. and adjusted the pH to 9.0-9.5 with ammonium hydroxide (65 ml, 20% w/w) at 25-30° C. to get a clear solution. Organic layer was separated, washed with water (100 ml) and dried over sodium sulfate. Thereafter, organic layer was concentrated at below 60° C. and tert.butanol (300 ml) was added to the residue. The reaction mass was heated to 70-75° C. Thereafter, powdered potassium hydroxide (32.35 g, 0.491 mole) was added and heated to reflux for completion of the reaction. Water (400 ml) was added and aqueous layer was separated and extracted with methylene chloride (500 ml). The combined organic layer was washed with water (200 ml) and dried over sodium sulfate. Methylene chloride solution was cooled to 2-5° C. and the pH adjusted to 1.2-1.4 with hydrochloric acid. The precipitated product was stirred for one hour and filtered, washed with methylene chloride to afford the title compound as white powder (90 g, 84.1% yield).

$^1$H NMR in DMSO-$d_6$ (δ in ppm): 4.03-4.05 (d, 2H), 7.31-7.74 (m, 10H), 8.53 (bs, 3H).

Stage II: Preparation of 4-[(α-N-pentanoylamino) cyclopentamidomethyl]-2'-carboxamidobiphenyl (XIV)

4-Aminomethyl-1,1'-biphenyl-2'-carboxamide hydrochloride (XIIIa) (200 g, 0.762 mole), N-pentanoylaminocyclopentanecarboxylic acid (XI) (162.4 g, 0.762 mole), 1-hydroxybenzotriazole (20.60 g, 0.152 mole) and dicyclohexylcarbodiimide (172.8 g, 0.8388 mole) were added to methylene chloride (5000 ml) at 25-30° C. Thereafter, diisopropylethylamine (109 g, 0.838 mole) was added and the reaction mixture was heated to 30-32° C. and maintained at this temperature for completion of the reaction. Thereafter, the contents were cooled to 20-30° C. and filtered the salts. The filtrate obtained was washed with water (2×400 ml) and concentrated to collect the methylene chloride (2000 ml). The slurry obtained was cooled to 2-5° C. and stirred for one hour. The solid was filtered, washed with precooled methylene chloride (400 ml), (0-5° C.) and dried to obtain the title compound as a white solid (272 g, 84.5% yield).

$^1$H NMR in DMSO-$d_6$ (δ in ppm), 0.83-0.88 (t, 3H), 1.22-1.29 (m, 2H), 1.45-1.50 (m, 2H), 1.62 (m, 4H), 1.87-2.11 (m, 4H), 2.13-2.16 (t, 2H), 4.28-4.30 (d, 2H), 7.22-7.48 (m, 10H), 7.89 (bs, 1H), 8.02-8.06 (t, 1H). Mass (+ve ion mode): 422.

Stage III: Preparation of 4-[(α-N-pentanoylamino) cyclopentamidomethyl]-2'-cyanobiphenyl (XII)

4-Aminomethyl-1,1'-biphenyl-2'-carbonitrile (VII) (10 g, 0.0408 mole), N-pentanoylaminocyclopentanecarboxylic acid (XI) (98.71 g, 0.0408 mole), 1-hydroxybenzotriazole (1.10 g, 0.0081 mole) and dicyclohexylcarbodiimide (9.27 g, 0.045 mole) were added to methylene chloride (200 ml) at 25-30° C. and thereafter, diisopropylethylamine (5.85, 0.045 mole) was added to the reaction mixture. The reaction mixture was heated to 30-32° C. and maintained at this temperature for completion of the reaction. Thereafter, the reaction mixture was cooled to 25-30° C. and filtered. The filtrate obtained was washed with water (2×20 ml) and concentrated to collect the methylene chloride (100 ml). The slurry obtained was cooled to 2-5° C. and stirred for one hour. The solid obtained was filtered, washed with precooled methylene chloride (20 ml, 0-5° C.) and dried to obtain the title compound as a white powder. (14 g, 84.9% yield).

$^1$H NMR in DMSO-$d_6$ (δ in ppm): 0.82-0.87 (t, 3H), 1.24-1.127 (q, 2H), 1.45-1.50 (sextet, 2H), 1.63 (m, 4H), 2.11-2.16 (t, 2H), 4.34-4.35 (d, 2H), 7.32-7.95 (m, 9H), 8.07-8.10 (t, 1H).

Stage IV: Preparation of 2-butyl-3-[p-(o-1H-tetrazol-5-ylphenyl)benzyl]-1,3-diazaspiro[4.4]non-1-en-4-one (Irbesartan)

Tributyltin chloride (47.80 g, 0.147 mole) and sodium azide (9.57 g, 0.147 mole) were stirred for 30 min at 15-30° C.

N,N-Dimethylformamide (6.90 g, 0.095 mole) was added and stirred for 30 min. Thereafter, 4-[(α-N-pentanoylaminocyclopentamidomethyl]-2'-carboxamidobiphenyl (XIV) (20 g, 0.0475 mole) was added followed by o-xylene (20 ml). The reaction mass was heated to 150-155° C. and stirred for completion of the reaction. The reaction mixture was cooled to 20° C., o-xylene (40 ml), methylene chloride (40 ml) were added followed by water (40 ml). Hydrochloric acid (4.95 g, 35% w/w) was added at 20-25° C. slowly in 30 min and the slurry obtained was stirred for 60 min. The solid was filtered, washed with 1:1 v/v mixture of o-xylene and methylene chloride (40 ml) and dried to get the crude Irbesartan as a pale yellow powder (18 g, 88.5% yield).

Example II

Stage I: Preparation of 4-[(α-N-pentanoylamino) cyclopentamidomethyl]-2'-carboxamidobiphenyl (XIV)

4-Aminomethyl-1,1'-biphenyl-2'-carboxamide (XIII) (10 g, 0.044 mole), N-pentanoylaminocyclopentanecarboxylic acid (XI) (9.42 g, 0.044 mole), 1-hydroxybenzotriazole (1.15 g, 0.0085 mole) and dicyclohexylcarbodiimide (9.20 g, 0.044 mole) were added to acetone (300 ml) at 25-30° C. The reaction mixture was heated to 30-32° C. and maintained at this temperature for 24 h. Thereafter, cooled the contents to 0-5° C. and filtered the salts. The filtrate obtained was concentrated, methylene chloride (100 ml) was added to the residue and stirred at 20-25° C. for 1 h. Solid was filtered, washed with precooled methylene chloride (20 ml, 0-5° C.) and dried to obtain the title compound as a white amorphous powder (12 g, 65% yield).

$^1$H NMR in DMSO-$d_6$ (δ in ppm), 0.83-0.88 (t, 3H), 1.22-1.29 (m, 2H), 1.45-1.50 (m, 2H), 1.62 (m, 4H), 1.87-2.11 (m, 4H), 2.13-2.16 (t, 2H), 4.28-4.30 (d, 2H), 7.22-7.48 (m, 10H), 7.89 (bs, 1H), 8.02-8.06 (t, 1H). Mass (+ve ion mode): 422.

Stage II: Preparation of 1-[(2'-carboxamidobiphenyl-4-yl)methyl]-2-n-butyl-4-spirocyclopentane-2-imidazolin-5-one (XV)

4-[(α-N-Pentanoylamino)cyclopentamidomethyl]-2'-carboxamidobiphenyl (XIV) (15 g, 0.036 mole) was suspended in o-Xylene (75 ml) and trifluoroacetic acid (8.20 g, 0.072 mole) was added at 25-30° C. The reaction mixture was heated to reflux (139-140° C.) and continued the stirring at reflux temperature for 15 h. Solvent was removed under reduced pressure and added ethyl acetate (150 ml) followed by water (75 ml) at 65-70° C. and cooled to 25-30° C. pH was adjusted to 9.0 with ammonium hydroxide (5 ml, 20% w/v) and stirred for 10 min. Aqueous layer was separated and extracted with ethyl acetate (15 ml). The combined ethyl acetate was washed with water (100 ml) at 25-30° C. and dried over sodium sulfate. Ethyl acetate extract was distillated off under reduced pressure at below 60° C. and toluene (75 ml) was added at 45-50° C. The slurry obtained was cooled to 0-5° C. and stirred for 30 min. Solid was filtered, washed with precooled toluene (15 ml, 5° C.) and dried to obtain the title compound as an off-white crystalline powder (10.85 g, 75.8% yield).

$^1$H NMR in DMSO-$d_6$ (δ in ppm), 0.79-0.83 (t, 3H), 1.26-1.29 (m, 2H), 1.48-1.53 (m, 2H), 1.67-1.85 (m, 8H), 4.71 (s, 2H), 7.15-7.66 (m, 10H). Mass (+ve ion mode): 404.5.

Stage III: Preparation of 1-[(2'-cyanobiphenyl-4-yl) methyl]-2-n-butyl-4-spirocyclopentane-2-imidazolin-5-one (IV)

1-[(2'-Carboxamidobiphenyl-4-yl)methyl]-2-n-butyl-4-spirocyclopentane-2-imidazolin-5-one (XV) (5 g, 0.0124 mole), pyridine (3.50 g, 0.044 mole), p-toluenesulfonylchloride (3.76 g, 0.0197 mole) were added respectively and heated the mixture to 70-75° C. Stirred the reaction mass at 70-75° C. for 1 h and cooled to 45-50° C. Ethyl acetate (50 ml) and water (50 ml) were added and stirred for 10 min. Aqueous layer was separated and extracted with ethyl acetate (25 ml) at 25-30° C. The combined ethyl acetate extract was washed with water (25 ml) and dried over sodium sulfate. Ethyl acetate was completely distilled under reduced pressure at below 50° C., the residue was dissolved in ethyl acetate (5 ml), cooled to −20° C. to −25° C. and kept overnight. The crystals formed were collected by filtration, washed with precooled ethyl acetate (5 ml, −10° C.) and dried to obtain the title compound as an off-white crystalline powder (2.20 g, 46% yield).

Stage 1V: Preparation of Irbesartan (I)

1-[(2'-Cyanobiphenyl-4-yl)methyl]-2-n-butyl-4-spirocyclopentane-2-imidazolin-5-one (IV) (2 g, 0.0052 mole), tributyltin chloride (2.42 g, 0.0074 mole), sodium azide (0.48 g, 0.0074 mole) were added respectively to o-xylene at 25-30° C. The mixture was heated to reflux temperature (144-146° C.) for 24 h and cooled to 20° C. Water (2 ml) was added followed by hydrochloric acid (1.8 ml, 15% w/v) at 18-20° C. and the slurry obtained was stirred for 15 min at 18-20° C. Solid was filtered, washed with water (6 ml) followed by toluene (6 ml, 40° C.). Finally, washed with water (6 ml). The wet solid (3.6 g) was suspended in water (15 ml) at 25-30° C. and adjusted the pH to 12.0 with 5% w/v aqueous sodium hydroxide (4.7 ml) in 5 min and treated with carbon for 30 minutes and filtered. The filtrate was washed with ethyl acetate (12 ml). pH of the aqueous layer was adjusted to 4.6-4.8 with hydrochloric acid (0.5 ml, 15% w/v) at 25-30° C. The slurry obtained was stirred for 30 min at 25-30° C. Solid was filtered, washed with water (5 ml, 35-40° C.) and dried to get the crude Irbesartan as an off-white powder (1.47 g, 66.2% yield).

Purification of Irbesartan Crude:

Irbesartan-crude, as obtained above (1.3 g), was suspended in ethanol (absolute alcohol, 15 ml) and heated to reflux temperature (82° C.) to get a clear solution. Carbon (90 mg) was added and stirred at 82° C. for 30 min. Carbon was filtered, washed with hot ethanol (5 ml, 60° C.). The filtrate was cooled to 25-30° C. and stirred for 1 h. Thereafter, cooled the slurry to 10-12° C. and stirred for 90 min at 10-12° C. Solid was filtered, washed with precooled ethanol (5 ml, 5° C.) and dried to obtain Irbesartan as a white crystalline powder (1.05 g).

Example III

Preparation of 4-[(α-N-pentanoylamino)cyclopentamidomethyl]-2'-carboxamidobiphenyl (XIV)

4-Aminomethyl-1,1'-biphenyl-2'-carboxamide hydrochloride (XIIIa) (15 g, 0.0571 mole), N-pentanoylaminocyclopentanecarboxylic acid (XI) (12.17 g, 0.057 mole), 1-hydroxybenzotriazole (1.5 g, 0.011 mole), diisopropylethylamine (8.17 g, 0.062 mole) and dicyclohexylcarbodiimide (12.95 g, 0.0062 mole) were added to methylene chloride (375 ml) at 25-30° C. and warmed the mixture to 32-33° C. Thereafter, stirring was continued for 6 h at 32-33° C. The slurry was cooled to 0-5° C. and filtered the salts. The filtrate was washed with saturated sodium bicarbonate solution (120 ml), concentrated to 75 ml volume under reduced pressure at below 50° C. and cooled to 0-5° C. Precipitated solid was filtered, washed with precooled methylene chloride (30 ml, 0° C.) and dried to give the title compound as white powder (18 g, 74.8% yield).

$^1$H NMR in DMSO-d$_6$ (δ in ppm), 0.83-0.88 (t, 3H), 1.22-1.29 (m, 2H), 1.45-1.50 (m, 2H), 1.62 (m, 4H), 1.87-2.16 (m, 6H), 4.28-4.30 (d, 2H), 7.22-7.62 (m, 10H), 7.89 (s, 1H), 8.06 (t, 1H). Mass (+ve ion mode): 422.

Example IV

Preparation of Irbesartan (I)

1-[(2'-Carboxamidobiphenyl-4-yl)methyl]-2-n-butyl-4-spirocyclopentane-2-imidazolin-5-one(XV) (10 g, 0.0248 mole), pyridine (5 g, 0.063 mole), p-toluenesulfonyl chloride (7.5 g, 0.039 mole) were added respectively and heated to 70-75° C. Thereafter, the reaction mixture was stirred at 70-75° C. for 1 h. o-Xylene (50 ml) and water (25 ml) were added at 70-75° C. and stirred for 10 min. Organic layer was separated, washed with water (25 ml) and dried over sodium sulfate. Sodium sulfate was washed with o-xylene (20 ml). Tributyltinchloride (11.70 g, 0.036 mole) and sodium azide (2.34 g, 0.036 mole) were added respectively to the xylene layer at 25-30° C. The reaction mixture was heated to reflux at 136-137° C. for 60 h. Thereafter, cooled to 10-15° C. and water (100 ml) was added. pH was adjusted to 11.5-12 with 10% w/w sodium hydroxide solution and stirred the reaction mass for 1 hour. Organic layer was separated and again extracted with water (100 ml). The combined aqueous layer was washed with ethyl acetate (2×25 ml) at 10-15° C. The aqueous layer pH was adjusted to 4.6-4.8 with 15% w/w hydrochloric acid at 25-30° C. Precipitated solid was filtered, washed with water (100 ml) and dried to obtain Irbesartan-crude as an off-white powder (5 g, 45% yield). It was purified as per the method given in Example I.

Example V

Preparation of Irbesartan (I)

1-[2'-Carboxamidobiphenyl-4-yl)methyl]-2-n-butyl-4-spirocyclopentane-2-imidazolin-5-one (XV) (5 g, 0.0124 mole) was added to a mixture of tributyl tin chloride (8.48 g, 0.026 mole) and o-xylene (5 ml) at 25-30° C. Sodium azide (1.69 g, 0.026 mole) was added to the above suspension and heated to reflux. Thereafter, reflux was continued till completion of the reaction. The reaction mass was cooled to 20-25° C. and o-xylene (10 ml), water (60 ml) were added followed by the addition of methylene chloride (60 ml) at 20-25° C. Hydrochloric acid (3 ml, 35% w/w) was added in 15 min at 20-25° C. and continued the stirring for 2 h at the same temperature. Thereafter, pH was adjusted to 4.5-4.8 with aqueous ammonia solution at 20-25° C. and continued the stirring for 2 h. Product was filtered, washed with a 1:3 v/v mixture of o-xylene and methylene chloride (10 ml). Product was dried at 70-75° C. under reduced pressure (10 mm Hg). The dried product was suspended in water (50 ml), heated to 50° C. and stirred for 30 min at 45-50° C. Product was filtered, washed with water (50 ml) and dried to afford Irbesartan as a white solid. (4.1 g, 77% yield).

Example VI

Preparation of 2-butyl-3-[p-(o-1H-tetrazol-5-ylphenyl)benzyl]-1,3-diazaspiro[4.4]non-1-en-4-one (Irbesartan)

Tributyltin chloride (12.11 g, 0.037 mole) and sodium azide (2.42 g, 0.037 mole) were stirred for 30 min at 15-30° C.

N,N-Dimethylformamide (2.00 g, 0.027 mole) was added and stirred for 30 min. Thereafter, 4-[α-N-pentanoylamino)cyclopentamidomethyl]-2'-cyanobiphenyl (XII) (10 g, 0.0248 mole) was added followed by o-xylene (10 ml). The reaction mass was heated to 150-155° C. and stirred for completion of the reaction. The reaction mixture was cooled to 20° C., and a mixture of o-xylene (20 ml), methylene chloride (60 ml) and water (40 ml) were added. Thereafter hydrochloric acid was added to precipitate the solid and stirred for 1 hr. The solid obtained was filtered, washed with 1:1 v/v mixture of o-xylene and methylene chloride (20 ml) and dried to get the crude Irbesartan as pale yellow powder (9.55 g, 90% yield).

We claim:

1. A single step process for the preparation of 2-butyl-3-[p-(o-1H-tetrazol-5-ylphenyl)benzyl]-1,3-diazaspiro[4.4]non-1-en-4-one (Irbesartan) of Formula I, Formula I

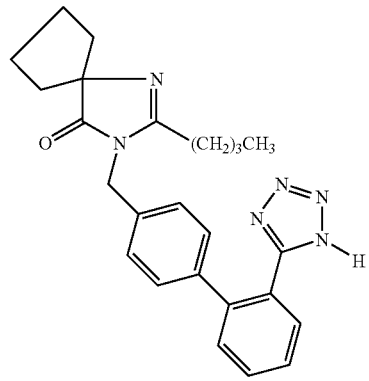

which comprises reacting the compound of Formula (XVI)

Formula XVI

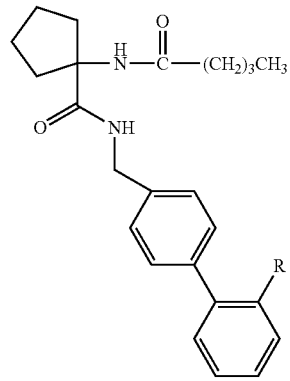

wherein R represents —CN or —CONH$_2$ groups with trialkyltin chloride and alkaline azide in an organic solvent to produce compound of Formula I.

2. The process according to claim 1, wherein the trialkyltin chloride is tributyltin chloride.

3. The process according to claim 1, wherein the alkaline azide is selected from sodium azide, potassium azide, more preferably sodium azide.

4. The process according to claim 1, wherein solvent is selected from aromatic hydrocarbons, polar aprotic organic solvents or mixtures there of.

5. The process according to claim 4, wherein aromatic hydrocarbons selected from benzene, toluene, xylenes more preferably o-xylene.

6. The process according to claim 4, wherein the polar aprotic organic solvent employed is selected from dimethylformamide, N-methyl pyrrolidinone, more preferably dimethylformamide.

7. The process according to claim 1, further comprising a process step, wherein the compound of Formula (XVI), wherein R is CONH2, is prepared by condensing the compound of Formula (XIIIa)

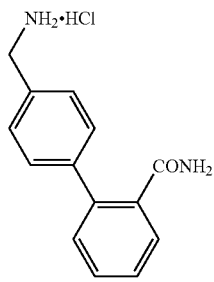

Formula XIIIa with N-pentanoylaminocyclopentanecarboxylic acid of Formula (XI)

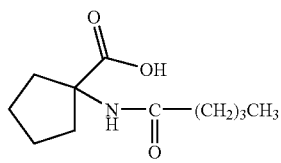

Formula XI in presence of condensing agent and optionally in presence of base in a solvent.

8. The process according to claim 7, wherein the condensing agent employed is selected from N,N'-dicyclohexylcarbodiimide, N-hydroxysuccinimide.

9. The process according to claim 7, wherein the condensation is carried out in presence of catalyst selected from 1-hydroxybenzotriazole.

10. The process according to claim 7, wherein base used is selected from organic bases such as triethylamine, diethylamine, diisopropylethylamine, butylamine, more preferably diisopropylethylamine.

11. The process according to claim 7, wherein solvent used in condensation step is selected from methylene chloride, chloroform, 1,2-dichloroethane, acetone, N,N-dimethyl formamide, dimethylacetamide, dimethylsulfoxide more preferably methylene chloride.

12. The process according to claim 1, wherein the compound of Formula (XVI),

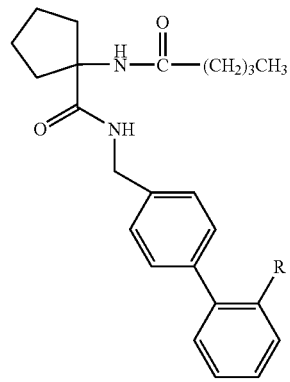

Formula XVI wherein R is —CN, is prepared by condensing a compound of Formula (XVII),

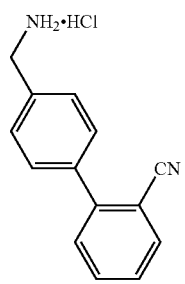

XVII with the N-pentanoylaminocyclopentanecarboxylic acid of Formula (XI)

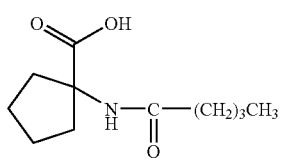

Formula XI in presence of condensing agent and optionally in presence of base in a solvent.

* * * * *